United States Patent
Heldreth

(10) Patent No.: US 7,022,123 B2
(45) Date of Patent: Apr. 4, 2006

(54) METHOD AND APPARATUS FOR CONTROLLING A SURGICAL BURR IN THE PERFORMANCE OF AN ORTHOPAEDIC PROCEDURE

(75) Inventor: Mark Alan Heldreth, Mentone, IN (US)

(73) Assignee: DePuy Products, Inc., Warsaw, IN (US)

(*) Notice: Subject to any disclaimer, the term of this patent is extended or adjusted under 35 U.S.C. 154(b) by 0 days.

(21) Appl. No.: 10/669,958

(22) Filed: Sep. 24, 2003

(65) Prior Publication Data

US 2004/0097948 A1 May 20, 2004

Related U.S. Application Data

(60) Provisional application No. 60/413,692, filed on Sep. 26, 2002.

(51) Int. Cl.
*A61B 17/16* (2006.01)
(52) U.S. Cl. .............................................. 606/80
(58) Field of Classification Search ............... 606/130, 606/1, 129, 159, 80, 170, 180, 424; 600/585, 600/424–427, 2; 607/60; 128/898; 604/22
See application file for complete search history.

(56) References Cited

U.S. PATENT DOCUMENTS

| 4,723,911 A | * | 2/1988 | Kurtz .......................... 433/27 |
| 5,269,785 A | * | 12/1993 | Bonutti ........................ 606/80 |
| 5,628,315 A | | 5/1997 | Vilsmeier et al. |
| 5,643,268 A | | 7/1997 | Vilsmeier et al. |
| 5,702,406 A | | 12/1997 | Vilsmeier et al. |
| 5,712,460 A | | 1/1998 | Carr et al. |
| 5,769,861 A | | 6/1998 | Vilsmeier |
| 5,880,976 A | | 3/1999 | DiGioia, III et al. |
| 5,889,834 A | | 3/1999 | Vilsmeier et al. |
| 5,995,738 A | | 11/1999 | DiGioia, III et al. |
| 6,002,859 A | | 12/1999 | DiGioia, III et al. |
| 6,017,354 A | | 1/2000 | Culp et al. |
| 6,084,979 A | | 7/2000 | Kanade et al. |
| 6,090,123 A | | 7/2000 | Culp et al. |
| 6,178,345 B1 | | 1/2001 | Vilsmeier et al. |
| 6,187,018 B1 | | 2/2001 | Sanjay-Gopal et al. |
| 6,205,411 B1 | | 3/2001 | DiGioia, III et al. |
| 6,223,067 B1 | | 4/2001 | Vilsmeier et al. |
| 6,329,778 B1 | | 12/2001 | Cupl et al. |
| 6,340,363 B1 | | 1/2002 | Bolger et al. |
| 6,351,659 B1 | | 2/2002 | Vilsmeier |
| 6,428,547 B1 | | 8/2002 | Vilsmeier et al. |
| 6,434,507 B1 | | 8/2002 | Clayton et al. |

(Continued)

FOREIGN PATENT DOCUMENTS

WO        WO 03/034922 A1        5/2003

OTHER PUBLICATIONS

International Search Report for PCT Application No. PCT/US03/29996, Jun. 3, 2004, 4 pages.

*Primary Examiner*—Eduardo O. Robert
*Assistant Examiner*—D. Jacob Davis
(74) *Attorney, Agent, or Firm*—Barnes & Thornburg LLP

(57) ABSTRACT

A method of operating a surgical burr during performance of an orthopaedic procedure includes monitoring the position of the surgical burr during the procedure and adjusting operation of the surgical burr based thereon. An orthopaedic surgical system is also disclosed.

10 Claims, 2 Drawing Sheets

U.S. PATENT DOCUMENTS

| | | |
|---|---|---|
| 6,514,259 B1 | 2/2003 | Picard et al. |
| 6,665,948 B1 * | 12/2003 | Kozin et al. .................. 33/833 |
| 2001/0027271 A1 * | 10/2001 | Franck et al. ............... 600/426 |
| 2001/0037064 A1 * | 11/2001 | Shahidi ...................... 600/429 |
| 2002/0038118 A1 | 3/2002 | Schoham |
| 2002/0077542 A1 * | 6/2002 | Vilsmeier et al. ........... 600/424 |
| 2002/0107522 A1 | 8/2002 | Picard et al. |
| 2002/0133160 A1 | 9/2002 | Axelson, Jr. et al. |
| 2003/0069585 A1 | 4/2003 | Axelson, Jr. et al. |
| 2003/0208296 A1 | 11/2003 | Brisson et al. |

\* cited by examiner

METHOD AND APPARATUS FOR CONTROLLING A SURGICAL BURR IN THE PERFORMANCE OF AN ORTHOPAEDIC PROCEDURE

This application claims priority to U.S. Provisional Patent Application Ser. No. 60/413,692 entitled "Method and Apparatus for Controlling a Surgical Burr in the Performance of an Orthopaedic Procedure" which was filed on Sep. 26, 2002 by Mark Heldreth, the entirety of which is expressly incorporated by reference herein.

FIELD OF THE DISCLOSURE

The present disclosure relates generally to a computer-aided surgical system for use in the performance of an orthopaedic procedure.

BACKGROUND

The increasing adoption of minimally invasive procedures in total joint arthroplasty is challenging current bone removal systems. As the envelope of the surgical site is contracted, the powered surgical tool has less volume in which to operate without damaging surrounding soft tissues or misshaping the bone. Current oscillating surgical saws have a large swing arc requiring a significant volume in which to operate. Current rotating burrs require less space but are more difficult to guide and navigate.

In situations where an oscillating saw is required to provide accurate guidance of bone resection and good bone apposition (i.e., an unguided burr has insufficient control to provide reproducible cuts), the design of the adjoining surfaces of the prostheses are constrained to be planar. This often results in more bone being removed than what is structurally required by the implant. Moreover, current orthopaedic procedures utilizing oscillating saws require the use of expensive jig systems (e.g., cutting blocks) to guide the position of the saw.

In an attempt to overcome one or more of these issues, a number of navigation systems for navigating a surgical burr have heretofore been developed. Such navigation systems have included active and passive robotic arms. In this approach, the arm either actively positions the burr in the correct position relative to the bone (irrespective of the surrounding soft tissue) or provides "passive" resistance to the burr being directed outside of the prescribed planned volume. In both cases, the burr is rigidly attached to a robotic jointed arm which may, in some cases, intrude into the sterile field and interrupt the surgeon's work flow. To date, adoption of such robotic technologies has been slow.

SUMMARY

According to one illustrative embodiment, there is provided a system for use in the performance of an orthopaedic surgical procedure. The system couples a computer aided surgical navigation system to the speed control of a surgical burr. As such, the position of the surgical burr may be tracked by the navigation system relative to a predetermined volume and/or geometry of bone to be removed as part of a pre-surgical plan. As the burr approaches the boundaries of the predetermined volume and/or geometry, the speed of the burr is modulated. The burr is thereby constrained to remove only the amount of bone previously planned by the surgeon. In addition, feedback is provided to the navigation system as to which bone has been removed. The volume and/or geometry of removed bone is then highlighted by the navigation system to the user (i.e., the surgeon).

According to another illustrative embodiment, there is provided a method of operating a surgical burr during performance of an orthopaedic procedure. The method includes monitoring the position of the surgical burr during the procedure and adjusting operation of the surgical burr based thereon. In certain implementations, the speed of the surgical burr is increased or decreased based on the position of the burr.

The above and other features of the present disclosure will become apparent from the following description and the attached drawings.

BRIEF DESCRIPTION OF THE DRAWINGS

The detailed description particularly refers to the accompanying figures in which.

DETAILED DESCRIPTION OF THE DRAWINGS

The present disclosure relates to a control system for coupling a computer aided surgical navigation system to the speed control of a surgical burr. To do so, the position of the surgical burr is tracked by the navigation system relative to a predetermined volume and/or geometry of bone to be removed as part of a pre-surgical plan. As the burr approaches the boundaries of the predetermined volume and/or geometry, the control system modulates the burr speed. The burr is thereby constrained to remove only the amount of bone previously planned by the surgeon. In addition, feedback is provided to the navigation system as to which bone has been removed. The volume and/or geometry of removed bone is then highlighted by the navigation system to the user (i.e., the surgeon).

Figure 1:
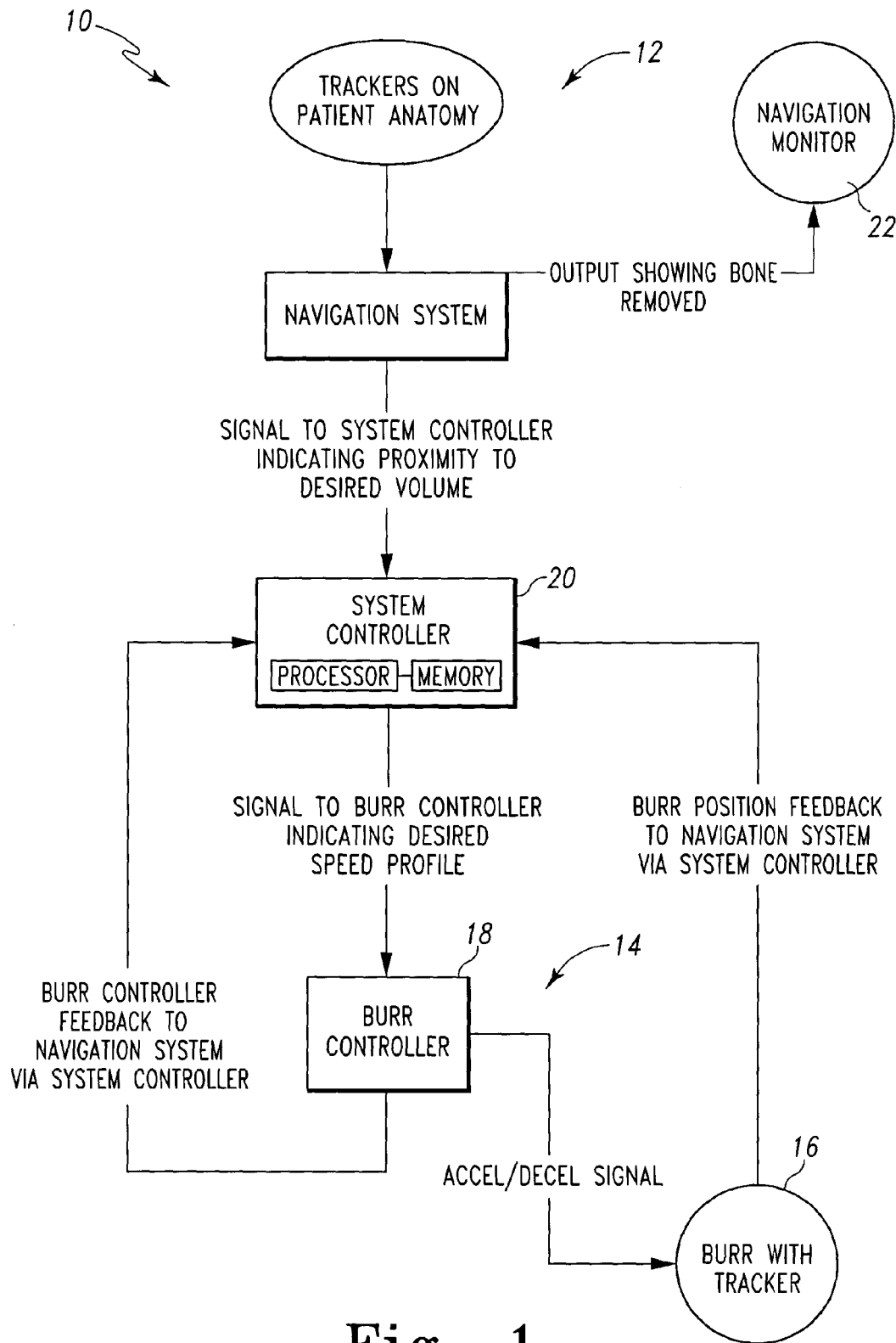
FIG. 1 is a simplified block diagram of a surgical control system for use in the performance of an orthopaedic surgical operation.

Referring now to FIG. 1, there is shown a surgical control system 10 having a computer-based surgical navigation system 12 and a computer-controlled surgical burr system 14. The control system 10 is operable to guide the position of a surgical burr 16 by tracking its position, while also controlling operation of the burr 16 based on its tracked position. In other words, the control system 10 monitors position of the burr 16 and then adjusts operation of the burr 16 based thereon.

The surgical navigation system 12 is configured to optically or electromagnetically track the position of the burr 16. As such, the surgical navigation system 12 may be embodied as any type of navigation system such as the surgical navigation systems commercially available from BrainLAB AG of Heimstetten, Germany. The navigation system 12 may also be embodied as any one or more of the navigation systems (or combination thereof) disclosed in U.S. Pat. Nos. 6,514,259; 6,434,507; 6,428,547; 6,424,856; 6,351,659; 6,223,067; 6,187,018; 6,178,345; 5,889,834; 5,769,861; 5,702,406; 5,643,268; and 5,628,315, along with U.S. Patent Application Publication No. 2002/0038118 A1, each of which is hereby incorporated by reference.

The burr system 14, on the other hand, may be embodied as any type of commercially available electronically-controlled surgical burr system. Moreover, the burr system 14 may be embodied as any one or more of the burr systems (or combination thereof) disclosed in U.S. Pat. Nos. 6,329,778;

6,090,123; 6,017,354; and 5,712,460, each of which is hereby incorporated by reference.

As shown in FIG. 1, both the components of the navigation system 12 and a controller 18 of the burr system 14 are electrically coupled to a system controller 20. The system controller 20 is, in essence, the master computer responsible for interpreting electrical signals sent by the navigation system 12 and for communicating with the burr controller 18 for controlling operation of the burr 16. For example, the system controller 20 of the present disclosure is operable to, amongst many other things, monitor output signals from the navigation system 12 indicative of the position of the burr 16 relative to a predetermined boundary or location. In essence, any of the numerous control signals generated by the navigation system 12 during operation thereof may be communicated to the system controller 20 for use by the controller 20 as a feedback mechanism for controlling operation of the burr 16. It should be appreciated that, if necessary, one or more software and/or hardware interfaces (not shown) may be utilized to facilitate the communication link between the navigation system 12, the burr controller 18, and the system controller 20. In other words, a software and/or hardware scheme may be utilized to handshake the systems associated with the navigation system 12 to the burr controller 18.

The system controller 20 includes a number of electronic components commonly associated with control units which are utilized in the control of electromechanical systems. For example, the system controller 20 may include, amongst other components customarily included in such devices, a processor such as a microprocessor and a memory device such as a hard drive or a programmable read-only memory device ("PROM") including erasable PROM's (EPROM's or EEPROM's). The memory device is utilized to store, amongst other things, instructions in the form of, for example, a software routine (or routines) which, when executed by the processor, allows the system controller 20 to control operation of the surgical burr 16.

The system controller 20 also includes an analog interface circuit (not shown). The analog interface circuit converts the output signals from the various components associated with the surgical system 10 into a signal which is suitable for presentation to an input of the microprocessor of the system controller 20. In particular, such an analog interface circuit, by use of an analog-to-digital (A/D) converter (not shown) or the like, converts the analog signals generated by the navigation system 12 into a digital signal for use by the microprocessor of the system controller 12. It should be appreciated that the A/D converter may be embodied as a discrete device or number of devices, or may be integrated into the microprocessor of the system controller 12. It should also be appreciated that if any one or more of the outputs signals from the navigation system 12 are in the form of a digital output signal, the analog interface circuit may be bypassed.

Similarly, the analog interface circuit of the system controller 18 converts signals from the microprocessor of the system controller 18 into an output signal which is suitable for presentation to the burr controller 18. In particular, the analog interface circuit, by use of a digital-to-analog (D/A) converter (not shown) or the like, converts the digital signals generated by the microprocessor into analog signals for use by the burr controller 18. It should be appreciated that, similar to the A/D converter described above, the D/A converter may be embodied as a discrete device or number of devices, or may be integrated into the microprocessor of the system controller 20. It should also be appreciated that if the burr controller 18 is operable on a digital input signal, the analog interface circuit may be bypassed.

The data transmission from the navigation system 12 to the system controller 20 may be by hardwire (either remote or resident on the navigation system 12) or wireless such as by use of a radio frequency transmission. Likewise, the data transmission from the system controller 20 to the burr controller 18 may be by hardwire (either remote or resident on the controller 12) or wireless such as by use of a radio frequency transmission.

The system controller 20 monitors the output from the navigation system 12 as to the relative position of the burr to the bone at a sampling rate in the range of, for example, 1000 hz to 1 hz. The relative position of the burr 16 to the preplanned surgical profile is then utilized by the system controller 20 to adjust the burr speed based upon a preprogrammed acceleration/deceleration profile. Such a acceleration/deceleration response profile executed by the system controller 20 may be in the form of either a fixed relation or, alternatively, the profile may be altered by the user (e.g., the surgeon) by the use of a digital or analog electronic input device for modifying the profile characteristics.

Once the appropriate burr speed has been determined by the system controller 20, the controller 20 sends an output in the form of a modulating signal to the burr controller 18. Depending upon the design of the surgical burr system 14, the burr controller 18 may respond to the output from the system controller 20 by adjusting the electrical current applied to the burr motor, adjusting hydraulic pressure applied to the burr turbine, adjusting pneumatic pressure applied to the burr turbine, and/or actuating of an electromagnetic coupling/decoupling clutch between the burr and the burr turbine. In other words, the burr controller 18 utilizes the output signals from the system controller 20 to adjust operation of the burr 16. More specifically, based on output from the system controller 20, the burr controller 18 adjusts speed of the burr 16. Moreover, such control methods may be combined so as to provide for smooth acceleration/deceleration of the burr 16, along with rapid deceleration of the burr 16.

It should be appreciated from the above discussion that the control system 10 of the present disclosure may be utilized to control operation of the surgical burr 16 during performance of a surgical procedure. For example, during an orthopaedic surgical procedure, the position of the burr 16 may be compared to a predetermined (i.e., planned) working volume and/or geometry by the navigation system 12 during an orthopaedic surgical procedure. As the burr 16 approaches the predetermined working volume and/or geometry from the outside, a visual/audio cue on a burr hand piece begins to inform the surgeon of the same. As the burr 16 enters a specified distance from the volume and/or geometry boundary, such information is relayed to the burr controller 18 so that the burr controller 18 can execute a preprogrammed speed vs. distance algorithm thereby accelerating the burr 16. The burr 16 reaches full speed as it passes through the volume and/or geometry boundary. As the burr 16 begins to exit the working volume and/or geometry from the inside, a visual/audio cue is again generated for the surgeon and a deceleration process is initiated by the burr controller 18.

In addition, since the navigation system 12 is, by its design, tracking the burr 16 relative to the patient's anatomy, the system 12 is able to determine which volume and/or geometry of the bone has been removed. This information may be visually presented to the surgeon on a display monitor 22 thereby allowing the surgeon to monitor his or her progress relative to certain anatomical structures.

Hence, the system controller 20 utilizes inputs in the form of (1) position of the surgical burr 16 and bone anatomy as tracked by the navigation system 12, and (2) the predetermined volume and/or geometry of bone to be removed by the burr 12 as defined in the pre-operative plan and stored either in the navigation system 12 or the system controller 20. Armed with this data, the system controller 20 generates an electronic control signal which is communicated to the burr controller 18 thereby causing the burr controller 18 to operated the burr 16 at a preprogrammed burr speed (including a predetermined acceleration/deceleration rate) based upon the proximity and relative position of the burr 16 to the preplanned burring profile. Moreover, the control system also generates data indicative of the volume and/or geometry of bone actually removed by the burr 16 and presents such data as a visual representation to the surgeon via the display monitor 22.

Figure 2:
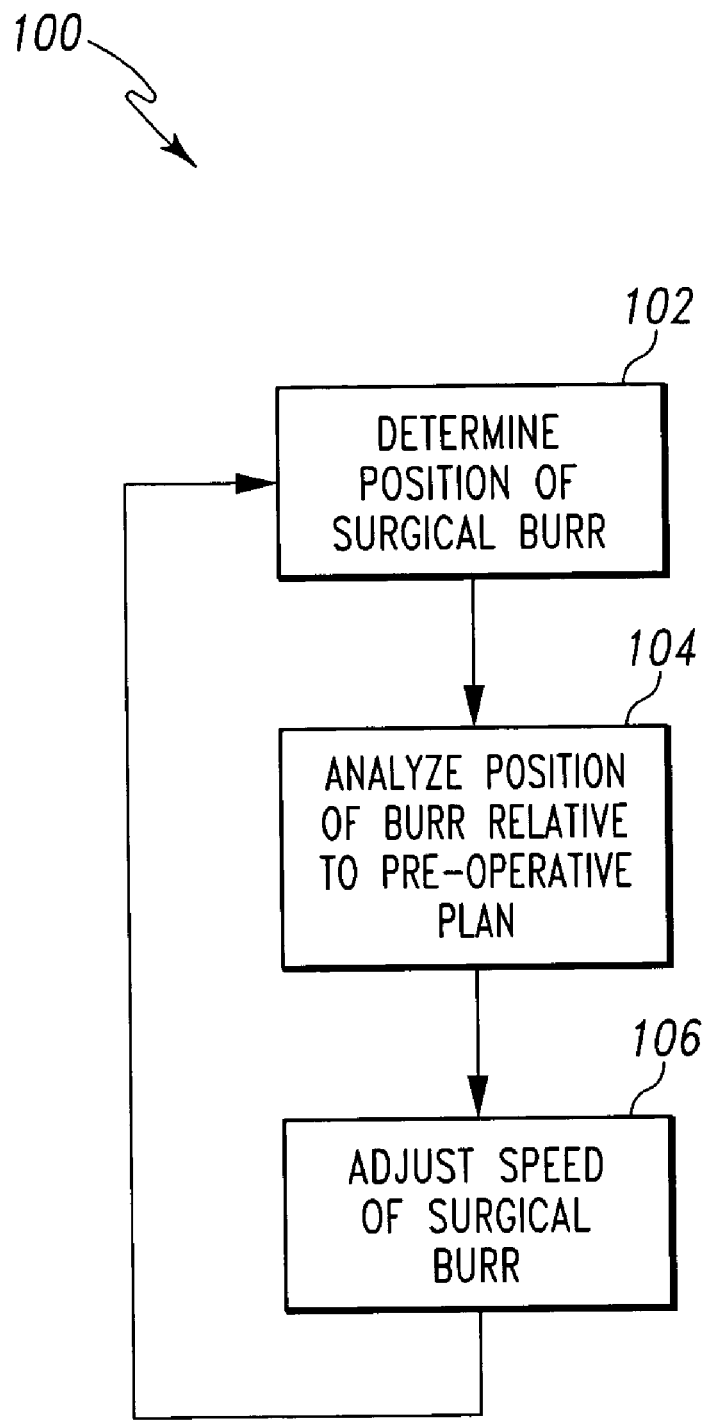
FIG. 2 is a flowchart of an exemplary control routine for operating the system of FIG. 1.

A flowchart of an exemplary control routine 100 for operating the surgical control system 10 is shown in FIG. 2. The routine 100 commences with step 102 in which the position of the surgical burr 16 is determined. In particular, the system controller 20 communicates with the navigation system 12 to determine the present location of the surgical burr 16 within the body of the patient. The routine 100 then advances to step 104.

In step 104, the present location of the surgical burr 16 (as determined in step 102) is analyzed in light of a predetermined volume and/or geometry of bone to be removed by the burr 12 as defined in the pre-operative plan and stored either in the navigation system 12 or the system controller 20. In an exemplary embodiment, a boundary is defined around the portion of the volume and/or geometry of the bone to be removed during generation of the pre-operative plan. An electronic file indicative of the image of such a boundary superimposed over the volume and/or geometry of the bone to be removed is stored in a memory device associated with either the navigation system 12 or the system controller 20. In step 104, the controller 20 analyzes the position of the surgical burr 16 relative to the boundary around the portion of the volume and/or geometry of the bone to be removed. Once the burr's position has been analyzed, an output signal is generated, and the routine 100 is advanced to step 106.

In step 106, the controller 20 adjusts operation of the surgical burr 16 based on the analysis of the burr's position. Specifically, based on the analysis of the position of the burr 16 (as analyzed in step 104), the speed of the surgical burr 16 is adjusted (e.g., either increased or decreased). For example, as the burr 16 enters a specified distance from the volume and/or geometry boundary, the system controller 20 communicates with the burr controller 18 so that the burr controller 18 can execute a preprogrammed speed vs. distance algorithm thereby accelerating the burr 16. The burr 16 reaches full speed as it passes through the volume and/or geometry boundary. As the burr 16 begins to exit the working volume and/or geometry from the inside, a deceleration process is initiated by the burr controller 18. If the burr 16 exits the boundary, the system controller 20 may communicate to the burr controller 18 to cease operation of the burr 16 so as to prevent the removal of bone material outside of the boundary. In any event, once the controller 20 has adjusted the speed of the surgical burr 16 in step 106, the routine 100 loops back to step 102 to continue closed-loop control of the operation of the burr 16 based on the position of the surgical burr 16.

It should be appreciated that the systems and methods described herein allow for feedback and guidance to be provided to the surgeon regarding the proper positioning of the burr without intruding on their work space and flow.

Moreover, the system and method described herein render the shaping of bone by burring more reproducible, hence, enabling bone conserving implants, while at the same time eliminating expensive bone cutting jigs. In particular, by providing a system for effectively navigating a surgical burr, the design of the orthopaedic implant to be implanted into the surgical site prepared by the burr may be configured to accommodate non-planar cuts while still providing for reproducible bone apposition. Moreover, by use of an accurately guided burr, the need for jig systems is eliminated.

In addition, the system and method described herein facilitates creation of an override function by causing the burr to shut off (or drop to a safe speed) when the burr is inadvertently maneuvered outside of the intended volume.

Moreover, the ability to simultaneously track the amount of bone removed enhances the surgeon's efficiency during the procedure.

While the disclosure is susceptible to various modifications and alternative forms, specific exemplary embodiments thereof have been shown by way of example in the drawings and has herein be described in detail. It should be understood, however, that there is no intent to limit the disclosure to the particular forms disclosed, but on the contrary, the intention is to cover all modifications, equivalents, and alternatives falling within the spirit and scope of the disclosure.

There are a plurality of advantages of the present disclosure arising from the various features of the apparatus and methods described herein. It will be noted that alternative embodiments of the apparatus and methods of the present disclosure may not include all of the features described yet still benefit from at least some of the advantages of such features. Those of ordinary skill in the art may readily devise their own implementations of an apparatus and method that incorporate one or more of the features of the present disclosure and fall within the spirit and scope of the present disclosure.

The invention claimed is:

1. An orthopaedic surgical system, comprising:
   a surgical burr,
   a surgical navigation system operable to determine position of the surgical burr during an orthopaedic procedure,
   a processor electrically coupled to both the surgical burr and the surgical navigation system, and
   a memory device electrically coupled to the processor, the memory device having stored therein a plurality of instructions which, when executed by the processor, cause the processor to:
   (a) communicate with the surgical navigation system to determine position of the surgical burr and generate an output signal in response thereto,
   (b) adjust operation of the surgical burr in response to generation of the output signal, and
   (c) generate a cue on the surgical burr in response to generation of the output signal.

2. The orthopaedic surgical system of claim 1, wherein the plurality of instructions, when executed by the processor, further cause the processor to adjust the speed of the surgical burr in response to generation of the output signal.

3. The orthopaedic surgical system of claim 1, wherein the plurality of instructions, when executed by the processor, further cause the processor to increase the speed of the surgical burr in response to generation of the output signal.

4. The orthopaedic surgical system of claim 1, wherein the plurality of instructions, when executed by the processor, further cause the processor to decrease the speed of the surgical burr in response to generation of the output signal.

5. The orthopaedic surgical system of claim 1, wherein the plurality of instructions, when executed by the processor, further cause the processor to determine the position of the surgical burr relative to an anatomical feature of a patient.

6. The orthopaedic surgical system of claim 1, wherein the plurality of instructions, when executed by the processor, further cause the processor to determine the position of the surgical burr relative to a predetermined boundary around an anatomical feature.

7. The orthopaedic surgical system of claim 6, wherein the plurality of instructions, when executed by the processor, further cause the processor to increase the speed of the surgical burr if the surgical burr is positioned within the predetermined boundary.

8. The orthopaedic surgical system of claim 6, wherein the plurality of instructions, when executed by the processor, further cause the processor to decrease the speed of the surgical bun if the surgical burr is positioned outside of the predetermined boundary.

9. The orthopaedic surgical system of claim 1, wherein the plurality of instructions, when executed by the processor, further cause the processor to generate a visual cue on the surgical burr in response to generation of the output signal.

10. The orthopaedic surgical system of claim 1, wherein the plurality of instructions, when executed by the processor, further cause the processor to generate an audio cue on the surgical burr in response to generation of the output signal.

* * * * *